US007955612B1

(12) United States Patent
Van Der Giessen et al.

(10) Patent No.: US 7,955,612 B1
(45) Date of Patent: Jun. 7, 2011

(54) INTRALUMINAL DEVICE, COATING FOR SUCH DEVICE, AND METHOD FOR PREPARING SAID DEVICE

(75) Inventors: Willem Johan Van Der Giessen, Rotterdam (NL); Helena M M Van Beusekom, Rotterdam (NL)

(73) Assignee: OrbusNeich Medical, Inc., Wilmington, DE (US)

( * ) Notice: Subject to any disclaimer, the term of this patent is extended or adjusted under 35 U.S.C. 154(b) by 1739 days.

(21) Appl. No.: 10/089,460

(22) PCT Filed: Oct. 2, 2000

(86) PCT No.: PCT/EP00/09658
§ 371 (c)(1),
(2), (4) Date: Apr. 1, 2002

(87) PCT Pub. No.: WO01/23016
PCT Pub. Date: Apr. 5, 2001

(30) Foreign Application Priority Data

Sep. 30, 1999 (EP) ..................................... 99203203

(51) Int. Cl.
*A61F 2/02* (2006.01)
(52) U.S. Cl. ........................................................ 424/423
(58) Field of Classification Search .................... 424/423
See application file for complete search history.

(56) References Cited

U.S. PATENT DOCUMENTS 4,963,146 A 10/1990 Li

FOREIGN PATENT DOCUMENTS

| EP | 0 945 145 A1 | 9/1999 |
| EP | 0945145 | 9/1999 |
| JP | 61 128974 | 6/1986 |
| JP | 61128974 | 6/1986 |
| WO | 95/31944 | 11/1995 |
| WO | WO 9531944 | 11/1995 |
| WO | 99/01167 | 1/1999 |
| WO | WO 9901167 | 1/1999 |

OTHER PUBLICATIONS

Cell Adhesion Proteins, Encyclopedia of Molecular Medicine, p. 1-12, 2002.*
A Schneider et al. "An Improved Method for Endothelial Cell Seeding on Polytetrafluoroethylene Small Caliber Vascular Grafts." *Journal of Vascular Surgery.* (Apr. 1992) 15 (4) 649-56. XP000884442 the whole document.
Aviva Schneider et al., "An Improved Method for Endothelial Cell Seeding on Polytetrafluoroethylene Small Caliber Vascular Grafts," *Journal of Vascular Surgery,* vol. 15, 1992, pp. 649-656.

* cited by examiner

*Primary Examiner* — Carlos A Azpuru
(74) *Attorney, Agent, or Firm* — Young & Thompson

(57) ABSTRACT

Disclosed is an intraluminal device, suitable for implantation in a body. The intraluminal device is provided with a coating which comprises: 50-97% heparan sulfate; 1-20% laminin; 0.2-15% type IV collagen. Furthermore a coating is disclosed, which coating is suitable for the above mentioned device, as well as a method for preparing such device, comprising the steps of: providing a intraluminal device for implantation in a body; preparing a composition, comprising, in about 50 mg/ml solvent: 50-97% heparan sulfate; 1-20% laminin; 0.2-15% type IV collagen; the solvent being a suitable buffer or water; dipping the intraluminal device in the composition; and drying the dipped intraluminal device.

17 Claims, No Drawings

INTRALUMINAL DEVICE, COATING FOR SUCH DEVICE, AND METHOD FOR PREPARING SAID DEVICE

This is a National Stage of PCT/EP00/09658 filed Oct. 2, 2000 that claims priority of European Application 99203203.7 filed Sep. 30, 1999.

BACKGROUND OF THE INVENTION

The present invention relates to an intraluminal device, suitable for implantation in a body, which intraluminal device is provided with a coating.

Intraluminal devices of the above mentioned type are generally known and applied. Such devices are for example applied in the treatment of blood vessel blockage in which the blocked blood vessel first is dilated, followed by placing a vascular prosthesis, in particular a stent, in the blood vessel in order to keep the vessel in the dilated state. This treatment does, however, give rise to several problems with regard to the vascular healing, as the natural healing process after such an operation is not regulated and as a consequence thereof undesirable local thrombosis can take place.

After the above implantation, the intraluminal device interacts with the vessel wall surface and the bloodstream. In a clinical setting the endothelialization of the intraluminal device is generally complete within two to three months after implantation. During this period the patient is at risk of thrombotic occlusion, undesired tissue growth, inflammation and vascular dysfunction.

There are several techniques available for controlling the above undesired effects of intraluminal devices, such as for example vascular stents. Thrombosis can passively be prevented by creating an inert surface which improves the surface characteristics that influence thrombosis. Such characteristics comprise, for example, charge, wettability and topography.

Thrombosis can also be prevented by binding one or more active components which inhibit thrombosis to the stent surface in order to actively prevent thrombosis. Examples of such components are prostaglandins, heparins, other thrombin inhibitors, or enzymes such as adenosine phosphatase.

Furthermore, thrombosis can be controlled by mimicking at the stent surface an already completed thrombotic response. This can be achieved by coating the stent surface with fibrin, thereby creating a controlled thrombus in vitro, as polymerized and stabilised fibrin is no longer thrombogenetic.

Thrombus formation can also be limited by disguising the stent surface with plasma proteins such as albumin, gamma globulins or phospholipids, which causes the skipping of certain phases in the proteinaceous—thrombotic and cellular—response.

The above mentioned coatings have an anti-proliferative effect; the growth velocity is inhibited in order to prevent thrombosis or restenosis.

A coating consisting of an extract of an extracellular biologically active basement membrane composition, derived for instance from the Engelbreth-Holm-Swarm tumor has been described in U.S. Pat. No. 4,829,000. However, it appears that this membrane is not suitable as a stent coating because it forms a thick shell on the stent surface. A. Schneider et al, J. Vasc. Surgery 15, 649 (1992) describe the application of a coating consisting of fibronectin whereupon bovine corneal endothelial cells grow. The cells were said to produce an extracellular matrix, and removed after 14 days. Thus coated polymer material was seeded with bovine aortic endothelial cells.

However, also this coating has a proliferative effect, viz. a large growth velocity of the cells but a big chance on thrombosis too. Moreover, this procedure is complicated and may suffer from bio-contamination.

SUMMARY OF THE INVENTION

The present invention aims to provide for an intraluminal device that after implantation in a body adds to an improvement of the process of vascular healing and prevents the formation of thrombosis, excessive tissue growth, inflammation and vascular dysfunction.

In order to achieve this, the present invention is directed to an intraluminal device comprising:
50-97% heparan sulfate;
1-20% laminin;
0.2-15% type IV collagen.

By providing an intraluminal device with a coating of the above specified composition a suitable substrate is provided on which endothelial cells can adhere. During the growth the endothelial cells create their own matrix upon which to grow and remain attached. Given that the normal endothelium is non-thrombogenic, providing a coating suitable for endothelial cell growth can shorten the period during which a patient is at risk of thrombotic occlusion.

All of the above components are also naturally present in the basement membrane of the blood vessel wall and are suitable for endothelial cell adhesion, growth and differentiation. Laminin can contribute to the binding properties of the coating to, for example DNA and RNA in gene therapy. Furthermore, type IV collagen adds to an improved attachment of the coating on the intraluminal device as well as a better attachment of the endothelial cells on the coated surface of the intraluminal device. Finally, the heparan sulfate is an important component as it has an effective anti-thrombogenic effect.

The coating according to the present invention provides a surface which is higher up in the natural healing cycle. The coating provides a fertile rich environment for endothelial cells and regulated thrombus formation. Thus, contrary to the coatings according to the prior art, the coating according to the present invention has a proliferative effect. As a result of the proliferative effect, the vascular wound healing is stimulated thereby decreasing the period during which thrombosis can occur and excessive tissue growth.

DESCRIPTION OF THE PREFERRED EMBODIMENTS

In a particular embodiment the coating comprises:
75-95% heparan sulfate;
3-10% laminin;
0.5-10% type IV collagen.

In a further preferred embodiment the coating comprises entactin and nidogen.

Said compounds add to the structural integrity of the coating and also improve the attachment of the—endothelial—cells to the intraluminal device coating.

In another advantageous embodiment the coating furthermore comprises a growth factor.

Growth factors in general stimulate the growth of—for example, endothelial—cells and therefore enhance the proliferative effect.

Preferably, the growth factor is chosen from the group consisting of bFGF, IGF, TGF-β and VEGF.

The different growth factors bFGF (basic fibroblast growth factor), IGF (insulin like growth factor), TGF-β (transforming growth factor-β), and VEGF (vascular endothelial growth factor) all add to the growth of specific components.

In order to prevent any risk of infection, the coating advantageously comprises an antibiotic.

In order to have an optimal effect the antibiotic should be a broad spectrum antibiotic, such as gentamycine.

In a preferred embodiment the coating of the intraluminal device according to the present invention comprises vitronectin.

Vitronectin offers a good basis for cell attachment; moreover it binds abciximab, GP 2b/3b inhibitor (ReoPro®) which is a compound with a known anti-thrombotic effect. By incorporating vitronectin in the intraluminal device coating and administering to a patient ReoPro® or other drugs that bind to vitronectin, thrombosis is even further prevented.

In a particular preferred embodiment of the intraluminal device according to the present invention, the coating comprises:
    85-95% heparan sulfate;
    5-6% laminin;
    3-4% type IV collagen;
    0.5-1.5% entactin and nidogen;
    0.001-1% growth factors;
    0.001-1% antibiotic.

In a preferred embodiment the intraluminal device comprises a vascular prosthesis such as a stent or a graft. The stent as well as the graft can be prepared from different materials known to the person skilled in the art.

The coated intraluminal device according to the present invention can furthermore be used as a basis for therapies such as, for example, drug delivery and gene therapy. Drugs can be bound to the coating such that the release thereof is controlled. As mentioned in the above, the presence of laminin in the coating improves the bonds which are desired and required in gene therapy. It is also possible to provide for one or more radioactive molecules in the coating in order to inhibit cell growth, if desired.

The present invention also relates to a coating suitable for application to an intraluminal device according to the present invention.

It will be clear that such coating may also be used on other substrates which can be implanted in a body.

The present invention also relates to a method for preparing an intraluminal device according to the above invention, comprising the steps of:
    providing an intraluminal device such as a wire of stainless steel, tantalum or polytetrafluoroethylene (PTFE) for implantation in a body;
    preparing a composition, comprising, in about 50 mg/ml solvent:
    50-97% heparan sulfate;
    1-20% laminin;
    0.2-15% type IV collagen;
    the solvent being a suitable buffer or water;
    dipping the intraluminal device in the composition; and
    drying the dipped intraluminal device.

The method as such is very simple and easy to perform and moreover is not time-consuming. The drying step can take place with or without heated or forced air drying.

Preferred embodiments of the method according to the present invention are those wherein the compositions to be prepared furthermore comprise one or more of the group consisting of a growth factor such as bFGF, IGF, TGF-β and VEGF, an antibiotic and vitronectin.

Preferably, a method for preparing a intraluminal device according to the above particular preferred embodiment, comprising the steps of:
    providing an intraluminal device such as a wire of stainless steel, tantalum or polytetrafluoroethylene (PTFE) for implantation in a body;
    preparing a composition, comprising, in about 50 mg/ml solvent:
    85-95% heparan sulfate;
    5-6% laminin;
    3-4% type IV collagen;
    0.5-1.5% entactin and nidogen;
    0.001-1% growth factors;
    0.001-1% antibiotic;
    the solvent being a suitable buffer or water;
    dipping the intraluminal device in the composition; and
    drying the dipped intraluminal device.

The present invention will be illustrated by the following, in no way the invention limiting, example.

Example

Helical coil, tantalum coronary stents were coated with the matrigel (n=2) as described in U.S. Pat. No. 4,829,000 or with a coating according to the present invention (n=2).

The stents were percutaneously implanted using sterile techniques in coronary arteries of farm-bred Yorkshire swines (ca. 30 kg) in such a way that one of each stent was placed per animal.

One of the two matrigel coated stents showed thrombotic occlusion within one week. The stent coated according to the present invention in the same animal was in a condition at autopsy. Mean neointimal thickness at one week was 24 μm (range 20-44 μm) in the matrigel coated stent and 14 μm (range 10-24 μm) in the stent coated according to the present invention.

In vitro platelet aggregation was measured in fresh, heparinized blood by measuring the impedance between the two electrodes. For this study the electrodes itself were coated with either matrigel or with the coating according to the present invention. Matrigel coating caused a decrease in impedance of 40% compared to a bare electrode. The coating with a composition according to the present invention caused a decrease of 60%. This implies a reduction of platelet aggregation in whole blood of the coating according to the present invention.

The invention claimed is:

1. An intraluminal device, suitable for implantation in a body, which device is provided with a coating, wherein the coating comprises:
    50-97% heparan sulfate;
    1-20% laminin; and
    0.2-15% type IV collagen.

2. The intraluminal device according to claim 1, wherein the coating comprises:
    75-95% heparan sulfate;
    3-10% laminin; and
    0.5-10% type IV collagen.

3. The intraluminal device according to claim 1, wherein the coating further comprises a growth factor.

4. The intraluminal device according to claim 3, wherein the growth factor is selected from the group consisting of bFGF, IGF, TGF-β and VEGF.

5. An intraluminal device, suitable for implantation in a body, the device being provided with a coating that comprises:
- 50-97% heparan sulfate;
- 1-20% laminin;
- 0.2-15% type IV collagen; and
- an antibiotic.

6. An intraluminal device, suitable for implantation in a body, the device being provided with a coating that comprises:
- 50-97% heparan sulfate;
- 1-20% laminin;
- 0.2-15% type IV collagen; and
- an antibiotic comprising gentamycine.

7. The intraluminal device according to claim 1, wherein the coating further comprises vitronectine.

8. The intraluminal device according to claim 1, wherein the coating comprises:
- 85-95% heparan sulfate;
- 5-6% laminin;
- 3-4% type IV collagen;
- 0.5-1.5% entactin and nidogen;
- 0.001-1% growth factors; and
- 0.001-1% antibiotic.

9. The intraluminal device according to claim 1, wherein the intraluminal device is a prosthesis that comprises a stent or a graft.

10. A coating suitable for the intraluminal device according to claim 1.

11. A method for preparing an intraluminal device, comprising the steps of:
- providing an intraluminal device for implantation in a body;
- preparing a composition, comprising, in about 50 mg/ml solvent:
  - 50-97% heparan sulfate;
  - 1-20% laminin;
  - 0.2-15% type IV collagen; and
  - the solvent being a suitable buffer or water;
- dipping the intraluminal device in the composition; and
- drying the dipped intraluminal device.

12. The method according to claim 11, wherein the composition further comprises entactin and nidogen.

13. The method according to claim 11, wherein the composition further comprises a growth factor, selected from the group consisting of bFGF, IGF, TGF-β and VEGF.

14. The method according to claim 11, wherein the composition further comprises an antibiotic.

15. The method according to claim 11, wherein the composition further comprises vitronectin.

16. The method according to claim 11, wherein the composition comprises:
- 85-95% heparan sulfate;
- 5-6% laminin;
- 3-4% type IV collagen;
- 0.5-1.5% entactin and nidogen;
- 0.001-1% growth factors; and
- 0.001-1% antibiotic.

17. The intraluminal device according to claim 1, wherein the coating further comprises entactin and nidogen.

* * * * *